United States Patent
Jensen et al.

(10) Patent No.: US 9,161,860 B2
(45) Date of Patent: Oct. 20, 2015

(54) REMOVABLE ABSORBENT PAD FOR TRANSPORTER

(75) Inventors: Ronald Jensen, Chicago, IL (US); Richard Beu, Yorba Linda, CA (US); Ann Tatoian, Glendora, CA (US)

(73) Assignee: Paper-Pak Industries, Laverne, CA (US)

( * ) Notice: Subject to any disclaimer, the term of this patent is extended or adjusted under 35 U.S.C. 154(b) by 0 days.

(21) Appl. No.: 12/862,291

(22) Filed: Aug. 24, 2010

(65) Prior Publication Data

US 2011/0046588 A1 Feb. 24, 2011

Related U.S. Application Data

(60) Provisional application No. 61/236,375, filed on Aug. 24, 2009.

(51) Int. Cl.
*A61F 13/15* (2006.01)
*A61G 1/00* (2006.01)
*A61G 1/048* (2006.01)
*A61G 1/04* (2006.01)

(52) U.S. Cl.
CPC . *A61F 13/15* (2013.01); *A61G 1/00* (2013.01); *A61G 1/04* (2013.01); *A61G 1/048* (2013.01)

(58) Field of Classification Search
CPC ............. A61G 1/00; A61G 1/01; A61G 1/04; A61G 1/048; A61F 13/15
USPC .............. 604/358, 360, 359; 5/625, 626, 628, 5/629, 89.1, 81.1, 484, 61, 502
See application file for complete search history.

(56) References Cited

U.S. PATENT DOCUMENTS

| | | | | |
|---|---|---|---|---|
| 1,263,918 A | * | 4/1918 | Miller | 296/19 |
| 3,905,054 A | * | 9/1975 | Windsor et al. | 5/86.1 |
| 5,061,235 A | * | 10/1991 | Hogan | 600/21 |
| 5,092,008 A | * | 3/1992 | Okubo | 5/484 |
| 5,575,025 A | | 11/1996 | Peters | |
| 5,733,272 A | * | 3/1998 | Brunner et al. | 604/359 |
| 6,009,558 A | * | 1/2000 | Rosch et al. | 2/212 |
| 6,231,556 B1 | * | 5/2001 | Osborn, III | 604/385.08 |
| 6,243,896 B1 | * | 6/2001 | Osuna et al. | 5/502 |
| 7,100,226 B1 | * | 9/2006 | Walton | 5/626 |
| 8,096,008 B1 | * | 1/2012 | Phillips | 5/626 |

(Continued)

FOREIGN PATENT DOCUMENTS

CA 2699374 A1 3/2009
GB 2213735 8/1989

(Continued)

OTHER PUBLICATIONS

Canadian Office Action dated Jan. 24, 2014 for Canadian application No. 2,713,617.

(Continued)

*Primary Examiner* — Lynne Anderson
*Assistant Examiner* — Bradley Philips
(74) *Attorney, Agent, or Firm* — Ohlandt, Greeley, Ruggiero & Perke, LLP

(57) ABSTRACT

An absorbent pad that can be removably connected to a transporter on which an injured person is carried is provided. Structures for removably attaching the absorbent pad to the transporter are described. Also provided are a transporter having a removable absorbent pad and a method for placing a removable absorbent pad on a transporter.

19 Claims, 1 Drawing Sheet

(56) References Cited

U.S. PATENT DOCUMENTS

| | | | |
|---|---|---|---|
| 2005/0055768 A1* | 3/2005 | Assink | 5/81.1 R |
| 2007/0056096 A1* | 3/2007 | Assink | 5/81.1 HS |
| 2007/0088392 A1* | 4/2007 | Skiba et al. | 607/2 |
| 2010/0263178 A1* | 10/2010 | Jensen et al. | 27/28 |

FOREIGN PATENT DOCUMENTS

| | | | |
|---|---|---|---|
| WO | WO 2008/109099 A1 | 9/2008 | |
| WO | WO 2009/036374 A1 | 3/2009 | |
| WO | WO 2009/091833 A1 | 7/2009 | |

OTHER PUBLICATIONS

Canadian Office Action dated Dec. 9, 2014 for Canadian application No. 2,713,617.

\* cited by examiner

1

REMOVABLE ABSORBENT PAD FOR TRANSPORTER

CROSS-REFERENCE TO RELATED APPLICATIONS

This application claims benefit of U.S. Provisional Application No. 61/236,375, filed on Aug. 24, 2009, which is incorporated by reference herein.

BACKGROUND OF THE DISCLOSURE

Field of the Disclosure

The present disclosure is directed to a transporter on which an injured person is carried having an absorbent media thereon.

SUMMARY OF THE DISCLOSURE

The present disclosure provides an absorbent pad that can be removably connected to a transporter on which an injured person is carried. The absorbent pad is made of an absorbent material or superabsorbent material that is suitable for absorbing a large amount of body fluids and/or water.

The absorbent pad is detachable from the transporter and can be replaced after use with a different absorbent pad.

The absorbent pad may be positioned on a transporter without being fastened or adhered to the transporter by inserting a portion of the absorbent pad in a complementary portion of the transporter. Alternatively, or in addition, the absorbent pad can be connected in place to the transporter by a fastener or an adhesive material.

The absorbent pad may optionally have one or more strengthening layers to improve the strength and resistance to tearing of the absorbent pad.

The absorbent pad can have an active agent that is a bactericide, fungicide, virucide, disinfectant, sanitizer, sterilizer, mildewstat, surfactant, and/or deodorizer.

The absorbent pad of the present disclosure can be positioned on or connected to any transporter that is suitable for transporting an injured person. Significantly, the absorbent pad is free to shift or to be adjusted when positioned on the transporter and thereby meet the needs of the injured person being transported.

DETAILED DESCRIPTION OF THE DISCLOSURE

Figures 1A, 1B:
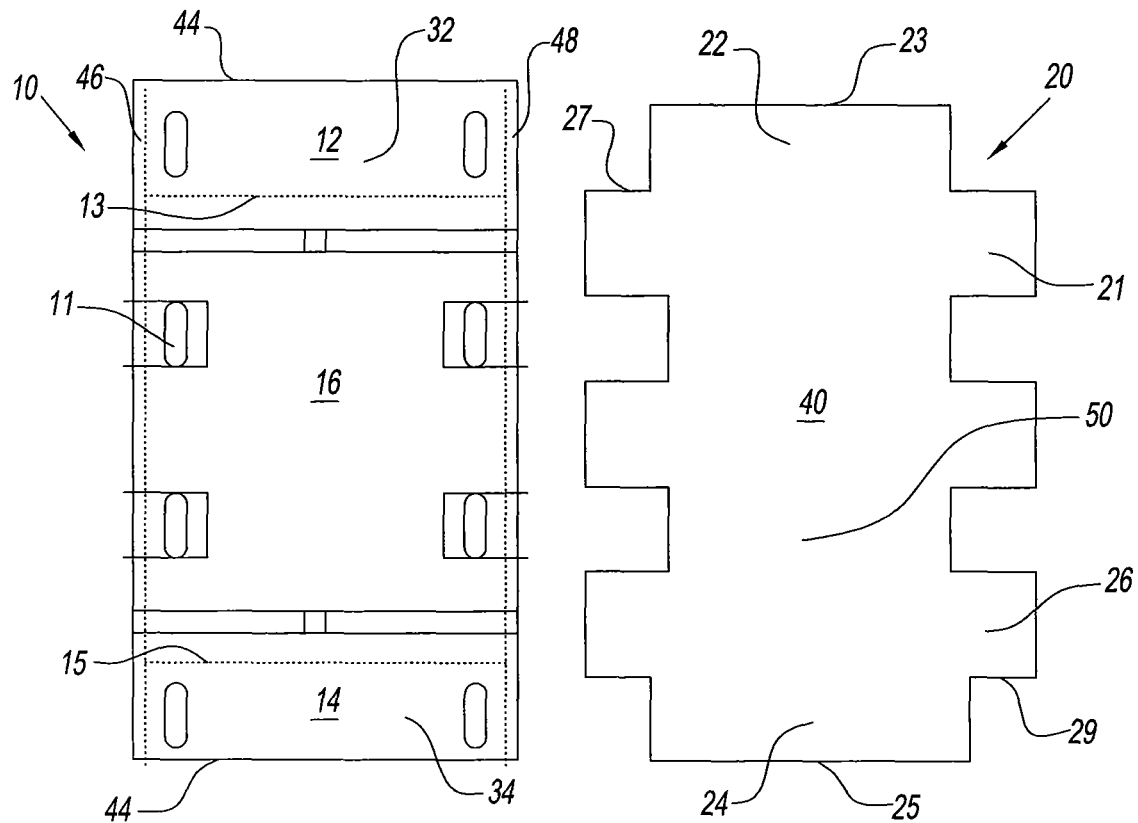
FIGS. 1A and 1B are top views of an exemplary embodiment of a transporter and an absorbent pad, respectively, of the present disclosure.

Referring to the Figures, and in particular, to FIG. 1A and FIG. 1B, there is provided an absorbent pad 20 that can be removably connected to transporter 10.

Absorbent pad 20 shown in FIG. 1B is positioned on a top surface of transporter 10 shown in FIG. 1A, to absorb blood and/or other body fluids from the person being transported.

Absorbent pad 20 can be any size and shape that permits it to be positioned, preferably removably, on transporter 10. As shown in the exemplary embodiment provided in FIG. 1A, transporter 10 has a top portion 12 and a bottom portion 14 that are delineated from main body 16 by stitch lines 13, 15, respectively. In a normal transporter 10, top portion 12 and bottom portion 14 are made by two or more layers and sewn or connected together along stitch lines 13, 15, respectively. In the present disclosure, one exemplary embodiment provides for the formation of a pocket 32 in top portion 12 and a pocket 34 in bottom portion 14. The pocket is formed by the materials of the transporter 10 but without stitch lines, so that the pocket is enclosed along horizontal edge 44 and the two vertical edges 46, 48.

Transporter 10 has hand-holds 11 along the sides thereof. Referring to FIG. 1B, absorbent pad 20 has a shape that covers a large portion of the top surface of transporter 10. Absorbent pad 20 can have one or more cut-outs 21, 26 that are preferably die-cut, to provide better access to the hand-holds by those persons carrying the transporter, and do not compromise the strength and integrity of the transporter 10. However, absorbent pad 20 can also be shaped without cut-outs 21, 26.

Absorbent pad 20 can be shaped to have a top segment 22 and/or a bottom segment 24. Top segment 22 extends from an upper edge 23 of absorbent pad 20 to anywhere to an uppermost edge 27 of a first cut-out 21. Likewise, bottom segment 24 extends from edge 25 of absorbent pad 20 to anywhere to a bottom-most edge 29 of cut-out 26. The area of absorbent pad 20 between top segment 20 and bottom segment 24 is body portion 40.

Figure 2:
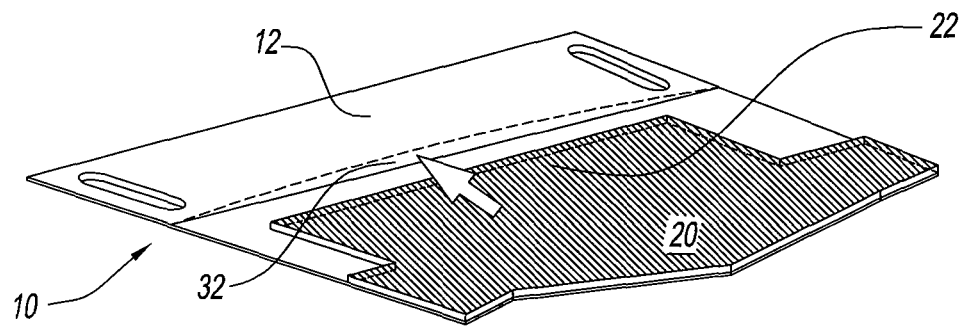
FIG. 2 is a perspective view illustrating an example of how an absorbent pad shown in FIG. 1B can be connected with a transporter shown in FIG. 1A.

As illustrated in FIG. 2, top segment 22 of absorbent pad 20 can be inserted into top pocket 32. Likewise, although not illustrated in FIG. 2, bottom segment 24 can be inserted into bottom pocket 34. Insertion of segments 22, 24 of absorbent pad 20 into their respective pockets secures the position of absorbent pad 20 on transporter 10, without adhesive or fasteners. Accordingly, body portion 40 is of a sufficient axial or vertical extant that top segment 22 and bottom segment 24 can reach and be inserted into their respective pockets 32, 34. Significantly, absorbent pad 20 is thereby free to shift or be adjusted when positioned on transporter 10 in order to meet the needs of the injured person being transported. After use, absorbent body 20 can be easily removed from transporter 10 as a single, individual piece.

Absorbent pad 20 can have a top layer (or body contact surface) 50 that does not adhere to the person, and that permits blood and other body fluids to pass through to the absorbent or superabsorbent layers in the absorbent pad. In this way, absorbent pad 20 keeps the injured person dry and comfortable, and reduces the risk of contamination.

Top layer 50 can be made of a polymer film, such as polyethylene or polypropylene film. Another embodiment of absorbent pad 20 has top layer 50 that is made of non-woven material, such as airlaid formed on a non-woven. Top layer 50 of absorbent pad 20 can also be made of a non-slip material, or treated with a non-slip agent or coating, to reduce movement or slipping of a person being carried on transporter 10.

Absorbent pad 20 has an absorbent material or superabsorbent material that is able to absorb large amounts of fluids, such as water, blood and/or other body fluids. Examples of absorbent and superabsorbent materials that can be used for absorbent pad include, but are not limited to, an airlaid, an airlaid composite, fluff pulp, bonding fiber, superabsorbent polymer (SAP), compressed SAP composite of SAP polymer granules adhered with one or more binders and/or plasticizers, compressed composite containing a percentage of short or microfiber materials, thermoplastic polymer fibers, thermoplastic polymer granules, cellulose powders, cellulose gels, an airlaid with SAP, a fibrous or foam structure that has been coated or impregnated with a SAP, an absorbent structure having one or more starch or cellulose based absorbents or containing superabsorbent material formed and/or crosslinked, or any combinations thereof. Superabsorbent materials used in the present disclosure can be used in various forms that include, but are not limited to, granular, fiber, liquid, superabsorbent hot melts, or any combinations thereof.

Absorbent pad 20 may also contain, or be treated with, a surfactant. The surfactant enhances absorption of fluids by absorbent pad 20. The amounts of surfactant used can be controlled to regulate the rate of wicking or absorption of absorbent pad 20. Examples of surfactants that can be used in the present disclosure include anionic surfactant, cationic surfactant, zwitterionic surfactant, and non-ionic surfactant.

Absorbent body 20 may have one or more strengthening layers to improve the strength and/or resistance to tearing of absorbent body 20. The one or more strengthening layers can be located on top of, below, or in between any portion of absorbent body 20. A strengthening layer of absorbent body 20 may be made of standard non-woven material, or melt-blown or spunlace composites. An exemplary embodiment is a strengthening layer made of polypropylene non-woven material or polypropylene/meltblown non-woven material.

Absorbent pad 20 and/or transporter 10 can also contain one or more active agent. The active agent can be positioned anywhere on and/or in absorbent pad 20 or transporter 10, to reduce infection and contamination of the transporter by microbial pathogens, and to reduce and/or eliminate odors. The active agent is preferably positioned in or on absorbent pad 20. The active agent includes, but is not limited to, a bactericide, fungicide, virucide, disinfectant, sanitizer, sterilizer, mildewstat, surfactant, deodorizer, and/or any combinations thereof. Active agents include, but are not limited to, a metal, metal compound, surface active agent, quaternary ammonium compound, organic acid, inorganic acid, salt, sulfite, biopolymer, synthetic polymer, chitin, chitosan, nisin, enzyme, arginate, diacetate, antioxidant, or any combinations thereof. An active agent may be present at absorbent pad 20 or transporter 10 in its active form, or present in an inactive form that becomes activated upon contact with fluids, such as body fluids from the person being carried, or water.

An adhesive material or one and/or more fasteners can be used to removably connect absorbent body 20 to transporter 10. Examples of adhesive materials or fasteners that can be used to connect absorbent pad 20 to transporter 10 include, but are not limited to, glue, two-sided tape, thread, button, snap, zipper, or a hook-and-loop interlocking device such as VELCRO® (Velcro Industries B.V. LLC Netherlands, Curacao, Netherlands Antilles). There may be one or more attachment points for the adhesive material or fastener. For example, if VELCRO® is used to removably connect absorbent pad 20 to a transporter, the male/female attachment points can be the underside of absorbent pad 20 and the top surface of transporter 10, respectively, or vice versa. After use, absorbent pad 20 can be completely detached from transporter 10 and disposed of, and a new absorbent pad positioned on the transporter in its place.

Transporter 10 can be any transporter suitable for carrying an injured person. Examples of transporters for which the removable absorbent pad 20 of the present disclosure can be used include: the disposable transporter disclosed in International Application No. PCT/US2008/0002907, and the lightweight transporter with anti-hypothermia structures disclosed in International Application No. PCT/US2008/076293, both of which are hereby incorporated by reference. The removable absorbent pad 20 of the present disclosure can also be of a size and shape to fit on attachments to a transporter, such as the absorbent head cover disclosed in International Application No. PCT/US2009/031007, which is hereby incorporated by reference. In addition, absorbent pad 20 can be used with transporters having structures that provide additional rigidity and support, including inflatable channels or chambers, and/or rigid bodies that are passed through holes or channels in the transporter, where such rigid bodies may be solid or hollow, and made of metal, polymer, and/or wood.

The disclosures herein are exemplary, and should not be construed as implying any particular limitation. It should be understood that various alternatives, combinations and modifications could be devised by those skilled in the art. The present disclosure is intended to embrace all such alternatives, modifications and variances that fall within the scope of the disclosure herein.

What is claimed is:

1. An absorbent pad removably secured to a transporter, the transporter having a top surface on which an injured person is carried and a plurality of hand-holds, the absorbent pad being positionable on the top surface of the transporter, the absorbent pad comprising:
   a top layer, wherein the top layer is permeable to blood or other body fluids and does not adhere to the person being carried on the transporter;
   an absorbent material for absorbing a large amount of blood or other body fluids from the injured person carried on the transporter; and
   a strengthening layer positioned between and adjacent the top layer and the absorbent material,
   wherein the absorbent pad is a single structure and has a plurality of cut-outs configured around the hand-holds of the transporter, and wherein the absorbent pad when positioned on the transporter is directly beneath the injured person being carried thereon, and
   wherein the absorbent pad is removable after use as a separate piece from the transporter.

2. The absorbent pad according to claim 1, wherein one of the plurality of cut-outs forms an edge of a segment of the absorbent pad.

3. The absorbent pad according to claim 2, wherein the segment is inserted in a pocket formed in an upper portion of the transporter to removably secure the absorbent pad on the transporter.

4. The absorbent pad according to claim 1, further comprising:
   an adhesive material or fastener, wherein the adhesive material or fastener removably connects the absorbent pad to the transporter.

5. The absorbent pad according to claim 1, wherein the top layer is disposed on the absorbent material.

6. The absorbent pad according to claim 5, wherein the blood or other body fluids are from the person carried on the transporter.

7. The absorbent pad according to claim 1, further comprising:
   an active agent.

8. The absorbent pad according to claim 7, wherein the active agent is selected from the group consisting of: bactericide, fungicide, virucide, sterilizer, mildewstat, and any combinations thereof.

9. The absorbent pad according to claim 7, wherein the active agent is inactive until activated by contact with water or the body fluids from the person being carried on the transporter.

10. The absorbent pad according to claim 1, wherein the absorbent pad is disposable after use.

11. A method of removably connecting the absorbent pad of claim 1 to the transporter, comprising:
placing the absorbent pad on the transporter,
wherein each of said plurality of cut-outs corresponds to a hand-hold of the transporter, and wherein each of said plurality of cut-outs forms an edge of a segment on the absorbent pad.

12. The method according to claim 11, wherein the absorbent pad is removably secured to the transporter by inserting said segment in a pocket of the transporter.

13. The method according to claim 11, wherein the absorbent pad is removably secured to the transporter by an adhesive material or fastener.

14. The absorbent pad according to claim 1, wherein the top layer is made of a polymer film.

15. The absorbent pad according to claim 1, wherein the top layer is made of a non-slip material or is coated with a non-slip agent or coating to reduce movement or slipping of the person being carried on the transporter.

16. The absorbent pad according to claim 1, wherein the absorbent pad contains or is treated with a surfactant to enhance absorption by the absorbent pad of the blood or other body fluids.

17. A transporter for carrying an injured person having a removable absorbent pad, the transporter comprising:
a backing substrate having a top side and a bottom side;
a hand-hold along an edge of the transporter;
an absorbent pad positioned on the top side of the backing substrate and directly beneath the injured person when the person is carried on the transporter, the absorbent pad comprising:
a top layer, the top layer having a cut-out portion configured to provide access to the hand-hold, wherein the top layer is permeable to blood or other body fluids and does not adhere to the person being carried on the transporter;
an absorbent or superabsorbent material for absorbing a large amount of blood or other body fluids from the injured person carried on the transporter; and
a strengthening layer positioned between and adjacent the top layer and the absorbent or superabsorbent material,
wherein the absorbent pad is a single structure that is removably connected to the transporter, and
wherein the absorbent pad is removable as a separate piece after use from the backing substrate, and replaceable with an unused absorbent pad positioned on the backing substrate.

18. The transporter according to claim 17, wherein the top side of the backing substrate further comprises a top pocket having a pocket opening across a widthwise extent of the transporter, and
wherein the pocket opening receives a top portion of the absorbent pad by insertion therein, thereby securing the absorbent pad to the top side of the backing substrate.

19. The transporter according to claim 17, further comprising an active agent in or on the backing substrate.

* * * * *